(12) United States Patent
Shah

(10) Patent No.: US 8,241,615 B2
(45) Date of Patent: Aug. 14, 2012

(54) WATER-RESISTANT SUNSCREEN COMPOSITION

(75) Inventor: Anil Shah, East Windsor, NJ (US)

(73) Assignee: L'Oreal S.A., Paris (FR)

( * ) Notice: Subject to any disclaimer, the term of this patent is extended or adjusted under 35 U.S.C. 154(b) by 88 days.

(21) Appl. No.: 12/906,455

(22) Filed: Oct. 18, 2010

(65) Prior Publication Data

US 2011/0091401 A1    Apr. 21, 2011

Related U.S. Application Data

(60) Provisional application No. 61/252,876, filed on Oct. 19, 2009.

(51) Int. Cl.
*A61K 8/04* (2006.01)
*A61K 31/74* (2006.01)
*A61Q 17/04* (2006.01)

(52) U.S. Cl. .......... 424/59; 424/78.03; 424/60; 514/761

(58) Field of Classification Search .................. None
See application file for complete search history.

(56) References Cited

U.S. PATENT DOCUMENTS

| | | | |
|---|---|---|---|
| 2,463,264 A | 3/1949 | Graenacher et al. |
| 4,931,210 A | 6/1990 | Takahashi et al. |
| 5,166,355 A | 11/1992 | Leistner et al. |
| 5,237,071 A | 8/1993 | Leistner et al. |
| 5,585,091 A | 12/1996 | Pelzer et al. |
| 6,093,385 A | 7/2000 | Habeck et al. |
| 6,159,455 A | 12/2000 | Habeck et al. |
| 6,387,355 B2 | 5/2002 | Heidenfelder et al. |
| 6,391,289 B2 | 5/2002 | Heidenfelder et al. |
| 6,436,373 B1 | 8/2002 | Habeck et al. |
| 6,534,647 B1 * | 3/2003 | Stevens et al. ............... 536/115 |
| 6,699,485 B1 * | 3/2004 | Pantini ........................ 424/401 |
| 2005/0013782 A1 | 1/2005 | Goppel et al. |

FOREIGN PATENT DOCUMENTS

| | | |
|---|---|---|
| DE | 197 26184 | 12/1998 |
| DE | 197 46 654 | 2/1999 |
| DE | 197 55 649 | 6/1999 |
| DE | 198 55 649 | 6/2000 |
| DE | 101 62 844 | 7/2003 |
| EP | 1 133 981 | 3/1985 |
| EP | 669323 | 8/1995 |
| EP | 0 832 642 | 4/1998 |
| EP | 893119 | 1/1999 |
| EP | 0 967 200 | 12/1999 |
| EP | 1 008 586 | 6/2000 |
| EP | 1027883 | 8/2000 |
| EP | 1 133 980 | 9/2001 |
| EP | 1300137 | 4/2003 |
| GB | 2 206 339 | 1/1989 |
| GB | 2303549 | 2/1997 |
| WO | 93-04665 | 3/1993 |

OTHER PUBLICATIONS

Mitchell L. Schlossman, Treated Pigments, New Ways to Impart Color on the Skin, Cosmetics & Toiletries, Feb. 1990, vol. 105, pp. 53-64, Tevco, Inc., South Plainfield, New Jersey.

* cited by examiner

*Primary Examiner* — Robert A Wax
*Assistant Examiner* — Sarah Park
(74) *Attorney, Agent, or Firm* — L'Oreal USA

(57) ABSTRACT

The present invention is directed to sunscreen composition comprising: (a) at least one oil- and water repellent emulsifier chosen from polyperfluoroethoxymethoxy difluoroethyl PEG phosphate; (b) at least one hydrophobically-modified emulsifier chosen from inulin lauryl carbamate; (c) at least one gelling agent; and (d) sunscreen actives, and wherein the composition is water-resistant, while not requiring the use of a film-former, and is a stable emulsion.

14 Claims, No Drawings

WATER-RESISTANT SUNSCREEN COMPOSITION

REFERENCE TO PRIOR APPLICATION

This application claims the benefit of priority under 35 U.S.C. §119(e) from U.S. provisional application Ser. No. 61/252,876, filed Oct. 19, 2009, incorporated herein by reference in its entirety.

FIELD OF THE INVENTION

The present invention is directed to a novel water-resistant sunscreen composition having exceptional skin-feel properties. More particularly, the invention is directed to a composition containing an association of at least two unique emulsifiers, together with a gelling agent and sunscreen actives, wherein the composition does not require the presence of film-formers in order to achieve water-resistance, while at the same time possessing exceptionally pleasant texture and skin-feel properties.

BACKGROUND OF THE INVENTION

Aging skin is the result of more than just chronological age. Skin is exposed to various environmental stresses, such as UV rays, which cause free radicals to form in the skin. Free radicals include, for example, singlet oxygen, hydroxyl radical, the superoxide anion, nitric oxide and hydrogen radicals. Free radicals attack DNA, membrane lipids and proteins, generating carbon radicals. These in turn react with oxygen to produce a peroxyl radical which may attack adjacent fatty acids to generate new carbon radicals. This process can lead to a chain reaction producing lipid peroxidation products. Damage to the cell membrane can result in loss of cell permeability, increased intercellular ionic concentration and/or decreased ability to excrete or detoxify waste products. The end result is a loss of elasticity of the skin and the appearance of wrinkles leading to premature ageing of the skin. This process is commonly referred to as photo-aging.

Thus, it is an object of the present invention to provide a composition and process for protecting cellular targets from aging and photo-damage caused by UV light, in general, and free radicals formed thereby, in particular.

The degree of UV protection afforded by a composition is directly related to the amount and type of sunscreen actives present therein. The more sunscreen actives present, the greater the degree of UV protection. However, in order to incorporate significant amounts of sunscreen actives into a composition, a large amount of emulsifiers have also needed to be used in order to make the composition stable so as to avoid separation and precipitation of ingredients. The use of significant amounts of emulsifiers, while making the composition more stable, detracts from the texture and feel of the composition when applied onto a keratinous substrate.

Thus, it is yet another object of the present invention to provide a sunscreen composition which provides a significant degree of UV protection, is stable, while at the same time having a light, non-oily texture and skin feel property.

Lastly, conventional sunscreen compositions are expected to possess water-resistance properties in order to inhibit the protective composition from being easily removed from a keratinous substrate surface by sweat and exposure to water. In order to achieve this function, film-formers are typically employed in the composition. By forming a film on the keratinous substrate surface, the sunscreen actives are more steadfastly held in place upon exposure to water. The use of film-formers, however, has a negative impact of the tactile properties of the composition, rendering it more tacky feeling.

Thus, it is another object of the present invention to provide a sunscreen composition which possesses water-resistance properties but does not require the use of a film-former.

SUMMARY OF THE INVENTION

The present invention is directed to a sunscreen composition containing:
1. at least one oil- and water-repellant emulsifier chosen from polyperfluoroethoxymethoxy difluoroethyl PEG phosphate;
2. at least one hydrophobically modified emulsifier chosen from inulin lauryl carbamate;
3. at least one gelling agent; and
4. sunscreen actives, and wherein the composition is water-resistant, while not requiring the use of a film-former, and is a stable emulsion.

The present invention is also directed to a method of protecting a keratinous substrate from UV rays by applying the above-disclosed composition onto a surface of the keratinous substrate.

DETAILED DESCRIPTION OF THE INVENTION

Other than in the operating examples, or where otherwise indicated, all numbers expressing quantities of ingredients and/or reaction conditions are to be understood as being modified in all instances by the term "about".

A "physiologically acceptable medium" means a medium which is not toxic and can be applied to the skin, lips, hair, scalp, lashes, brows, nails or any other cutaneous region of the body. The composition of the invention may especially constitute a cosmetic or dermatological composition.

The phrase "stable emulsion" refers to a composition that does not undergo phase separation up to a temperature of 45 degrees C.

The present invention is directed to the surprising and unexpected discovery that a highly effective sunscreen composition having water-resistant properties as well as exceptional texture and skin-feel properties can be formulated without the need for having to employ a conventional film-forming ingredient. A sunscreen composition possessing these properties can be obtained by combining a water-repellent emulsifier, with a hydrophobically-modified emulsifier, a gelling agent and sunscreen actives.

Oil- and Water-Repellent Emulsifier

The at least one oil- and water-repellent emulsifier of the present invention is a polyperfluoroethoxymethoxy difluoroethyl PEG phosphate, commercially available from Arch Chemicals under the tradename Fomblin HC/P2-1000®®.

The at least one oil- and water-repellent emulsifier is typically employed in an amount of from about 0.05 to about 1.0% by weight, such as from about 0.05 to about 0.8% by weight, and from about 0.05 to about 0.5% by weight, based on the total weight of the composition.

Hydrophobically-Modified Emulsifier

Suitable hydrophobically-modified emulsifiers include, for example, inulin lauryl carbamate, commercially available from Beneo Orafti under the tradename Inutec SP1.

The at least one hydrophobically-modified emulsifier is typically employed in an amount of from about 0.1 to about 2.0% by weight, such as from about 0.3 to about 1.5% by weight, and from about 0.5 to about 1.0% by weight, based on the total weight of the composition.

Gelling Agent

Suitable hydrophilic gelling agents include, but are not limited to, carboxyvinyl polymers such as the Carbopol products (carbomers) and the Pemulen products (acrylate/C10-C30-alkylacrylate copolymer); polyacrylamides, for instance the crosslinked copolymers sold under the names Sepigel 305 (CTFA name: polyacrylamide/C13-14 isoparaffin/Laureth 7) or Simulgel 600 (CTFA name: acrylamide/sodium acryloyldimethyltaurate copolymer/isohexadecane/polysorbate 80) by the company SEPPIC; 2-acrylamido-2-methylpropanesulfonic acid polymers and copolymers, which are optionally crosslinked and/or neutralized, for instance the poly(2-acrylamido-2-methylpropanesulfonic acid) sold by the company Hoechst under the trade name "Hostacerin AMPS" (CTFA name: ammonium polyacryldimethyltauramide); cellulose-based derivatives such as hydroxyethylcellulose; polysaccharides and especially gums such as xanthan gum; and mixtures thereof.

Lipophilic thickeners that may be mentioned include modified clays such as hectorite and its derivatives, for instance the products sold under the name bentone.

A particularly preferred gelling agent for use in the present invention is ammonium acryloyldimethyltaurate/steareth-25 methacrylate crosspolymer, commercially available from Clariant under the tradename Aristoflex HMS.

The gelling agent will typically be employed in an amount of from about 0.05 to about 1.5% by weight, such as from about 0.08 to about 1.0% by weight, and from about 0.1 to about 0.5% by weight, based on the total weight of the composition.

Sunscreen Actives

Examples thereof include, but are not limited to, butyl methoxydibenzoylmethane; anthranilates; salicylic derivatives; camphor derivatives; benzophenone derivatives; $\beta,\beta$-diphenylacrylate derivatives; triazine derivatives; benzotriazole derivatives; benzalmalonate derivatives; benzimidazole derivatives; imidazolines; bis-benzazolyl derivatives as described in patents EP 669 323 and U.S. Pat. No. 2,463,264; p-aminobenzoic acid (PABA) derivatives; methylenebis(hydroxyphenylbenzotriazole) derivatives as described in patent applications U.S. Pat. No. 5,237,071, U.S. Pat. No. 5,166,355, GB 2 303 549, DE 197 26 184 and EP 893 119; benzoxazole derivatives such as those described in patent applications EP 0 832 642; EP 1 027 883, EP 1 300 137 and DE 101 62 844; screening polymers and screening silicones such as those described especially in patent application WO 93/04665; dimers derived from α-alkylstyrene, such as those described in patent application DE 198 55 649; 4,4-diarylbutadienes such as those described in patent applications EP 0 967 200, DE 197 46 654, DE 197 55 649, EP-A-1 008 586, EP 1 133 980 and EP 133 981, and mixtures thereof.

As examples of organic photoprotective agents, mention may be made of those denoted hereinbelow under their INCI name:

Butyl methoxydibenzoylmethane sold by A&E Connock (Perfumery & Cosmetics) LTD., also known as Avobenzone and also sold under the names "Eusolex 9020" sold by Merck KGaA/EMD Chemicals Inc., "Neo Heliopan" sold by Symrise, "Parsol 1789" sold by DSM Nuritional Products and "Oristar ABZ" sold by Orient Stars LLC.

Para-Aminobenzoic Acid Derivatives:
PABA,
Ethyl PABA,
Ethyl dihydroxypropyl PABA,
Ethylhexyl dimethyl PABA sold in particular under the name "Escalol 507" by ISP,
Glyceryl PABA, PEG-25 PABA sold under the name "Uvinul P25" by BASF.

Salicylic Derivatives:
Homosalate sold under the name "Eusolex HMS" by Rona/EM Industries,
Ethylhexyl salicylate sold under the name "Neo Heliopan OS" by Haarmann and Reimer,
Dipropylene glycol salicylate sold under the name "Dipsal" by Scher,
TEA salicylate sold under the name "Neo Heliopan TS" by Haarmann and Reimer.

$\beta,\beta$-Diphenylacrylate Derivatives:
Octocrylene sold in particular under the trade name "Uvinul N539" by BASF,
Etocrylene sold in particular under the trade name "Uvinul N35" by BASF.

Benzophenone Derivatives:
Benzophenone-1 sold under the trade name "Uvinul 400" by BASF,
Benzophenone-2 sold under the trade name "Uvinul D50" by BASF,
Benzophenone-3 or Oxybenzone sold under the trade name "Uvinul M40" by BASF,
Benzophenone-4 sold under the trade name "Uvinul MS40" by BASF,
Benzophenone-5,
Benzophenone-6 sold under the trade name "Helisorb 11" by Norquay,
Benzophenone-8 sold under the trade name "Spectra-Sorb UV-24" by American Cyanamid,
Benzophenone-9 sold under the trade name "Uvinul DS-49" by BASF,
Benzophenone-12
Diethylaminohydroxybenzoylhexyl benzoate sold under the trade name "Uvinul A Plus" by BASF, Benzylidenecamphor Derivatives:
3-Benzylidenecamphor manufactured under the name "Mexoryl SD" by Chimex,
4-Methylbenzylidenecamphor sold under the name "Eusolex 6300" by Merck,
Benzylidenecamphorsulfonic acid manufactured under the name "Mexoryl SL" by Chimex,
Camphor benzalkonium methosulfate manufactured under the name "Mexoryl SO" by Chimex,
Terephthalylidenedicamphorsulfonic acid manufactured under the name "Mexoryl SX" by Chimex,
Polyacrylamidomethylbenzylidenecamphor manufactured under the name "Mexoryl SW" by Chimex.

Phenylbenzimidazole Derivatives:
Phenylbenzimidazolesulfonic acid sold in particular under the trade name "Eusolex 232" by Merck,
Disodium phenyl dibenzimidazole tetrasulfonate sold under the trade name "Neo Heliopan AP" by Haarmann and Reimer.

Phenylbenzotriazole Derivatives:
Drometrizole trisiloxane sold under the name "Silatrizole" by Rhodia Chimie,
Methylenebis(benzotriazolyl)tetramethylbutylphenol sold in solid form under the trade name "MIXXIM BB/100" by Fairmount Chemical, or in micronized form as an aqueous dispersion under the trade name "Tinosorb M" by Ciba Specialty Chemicals.

Triazine Derivatives:
-Bis(ethylhexyloxyphenol)methoxyphenyl triazine sold under the trade name "Tinosorb S" by Ciba-Geigy,
Ethylhexyltriazone sold in particular under the trade name "Uvinul T150" by BASF, Diethylhexylbutamidotriazone sold under the trade name "Uvasorb HEB" by Sigma 3V, 2,4,6-tris(diisobutyl 4'-aminobenzalmalonate)-s-triazine.

Anthranilic Derivatives:

Menthyl anthranilate sold under the trade name "Neo Heliopan MA" by Haarmann and Reimer.

Imidazoline Derivatives:

Ethylhexyldimethoxybenzylidenedioxoimidazoline propionate.

Benzalmalonate Derivatives:

Polyorganosiloxane containing benzalmalonate functions, for instance Polysilicone-15, sold under the trade name "Parsol SLX" by Hoffmann LaRoche 4,4-Diarylbutadiene Derivatives:

1,1-Dicarboxy(2,2'-dimethylpropyl)-4,4-diphenyl-butadiene

Benzoxazole Derivatives:

2,4-bis[5-(1-dimethylpropyl)benzoxazol-2-yl(4-phenyl)imino]-6-(2-ethylhexyl)imino-1,3,5-triazine sold under the name Uvasorb K2A by Sigma 3V and mixtures thereof.

Examples of mineral photoprotective agents are chosen from pigments and even more preferably nanopigments (mean size of the primary particles: generally between 5 nm and 100 nm and preferably between 10 nm and 50 nm) of treated or untreated metal oxides such as, for example, nanopigments of titanium oxide (amorphous or crystallized in rutile and/or anatase form), of iron oxide, of zinc oxide, of zirconium oxide or of cerium oxide.

The treated nanopigments are pigments that have undergone one or more surface treatments of chemical, electronic, mechanochemical and/or mechanical nature with compounds as described, for example, in Cosmetics & Toiletries, February 1990, Vol. 105, pp. 53-64, such as amino acids, beeswax, fatty acids, fatty alcohols, anionic surfactants, lecithins, sodium, potassium, zinc, iron or aluminium salts of fatty acids, metal (titanium or aluminium) alkoxides, poly-ethylene, silicones, proteins (collagen or elastin), alkanolamines, silicon oxides, metal oxides, sodium hexametaphosphate, alumina or glycerol.

The treated nanopigments may more particularly be titanium oxides treated with:

silica and alumina, such as the products "Microtitanium Dioxide MT 500 SA" and "Microtitanium Dioxide MT 100 SA" from the company Tayca, and the products "Tioveil Fin", "Tioveil OP", "Tioveil MOTG" and "Tioveil IPM" from the company Tioxide, alumina and aluminium stearate, such as the product "Microtitanium Dioxide MT 100 T" from the company Tayca, alumina and aluminium laurate, such as the product "Microtitanium Dioxide MT 100 S" from the company Tayca, iron oxides and iron stearate, such as the product "Microtitanium Dioxide MT 100 F" from the company Tayca, silica, alumina and silicone, such as the products "Microtitanium Dioxide MT 100 SAS", "Microtitanium Dioxide MT 600 SAS" and "Microtitanium Dioxide MT 500 SAS" from the company Tayca, sodium hexametaphosphate, such as the product "Microtitanium Dioxide MT 150 W" from the company Tayca, octyltrimethoxysilane, such as the product "T-805" from the company Degussa, alumina and stearic acid, such as the product "UVT-M160" from the company Kemira, alumina and glycerol, such as the product "UVT-M212" from the company Kemira, alumina and silicone, such as the product "UVT-M262" from the company Kemira.

Other titanium oxide nanopigments treated with a silicone are preferably $TiO_2$ treated with octyltrimethylsilane and for which the mean size of the elementary particles is between 25 and 40 nm, such as the product sold under the trade name "T805" by the company Degussa Silices, $TiO_2$ treated with a polydimethylsiloxane and for which the mean size of the elementary particles is 21 nm, such as the product sold under the trade name "70250 Cardre UF TiO2SI3" by the company Cardre, anatase/rutile $TiO_2$ treated with a polydimethylhydrogenosiloxane and for which the mean size of the elementary particles is 25 nm, such as the product sold under the trade name "Microtitanium Dioxide USP Grade Hydrophobic" by the company Color Techniques.

The uncoated titanium oxide nanopigments are sold, for example, by the company Tayca under the trade names "Microtitanium Dioxide MT 500 B" or "Microtitanium Dioxide MT 600 B", by the company Degussa under the name "P 25", by the company Wackher under the name "Oxyde de titane transparent PW", by the company Myoshi Kasei under the name "UFTR", by the company Tomen under the name "ITS" and by the company Tioxide under the name "Tioveil AQ".

The uncoated zinc oxide nanopigments are, for example:

those sold under the name "Z-Cote" by the company Sunsmart;

those sold under the name "Nanox" by the company Elementis;

those sold under the name "Nanogard WCD 2025" by the company Nanophase Technologies.

The coated zinc oxide nanopigments are, for example:

those sold under the name "Zinc Oxide CS-5" by the company Toshibi (ZnO coated with polymethylhydrogenosiloxane);

those sold under the name "Nanogard Zinc Oxide FN" by the company Nanophase Technologies (as a 40% dispersion in Finsolv TN, $C_{12}$-$C_{15}$ alkyl benzoate);

those sold under the name "Daitopersion ZN-30" and "Daitopersion ZN-50" by the company Daito (dispersions in cyclopolymethylsiloxane/oxyethylenated polydimethylsiloxane, containing 30% or 50% of nanozinc oxides coated with silica and polymethylhydrogenosiloxane);

those sold under the name "NFD Ultrafine ZNO" by the company Daikin (ZnO coated with perfluoroalkyl phosphate and copolymer based on perfluoroalkylethyl as a dispersion in cyclopentasiloxane);

those sold under the name "SPD-Z1" by the company Shin-Etsu (ZnO coated with silicone-grafted acrylic polymer, dispersed in cyclodimethylsiloxane);

those sold under the name "Escalol Z100" by the company ISP (alumina-treated ZnO dispersed in an ethylhexyl methoxycinnamate/PVP-hexadecene/methicone copolymer mixture);

those sold under the name "Fuji ZNO-SMS-10" by the company Fuji Pigment (ZnO coated with silica and polymethylsilsesquioxane);

those sold under the name "Nanox Gel TN" by the company Elementis (ZnO dispersed at a concentration of 55% in $C_{12}$-$C_{15}$ alkyl benzoate with hydroxystearic acid polycondensate).

The uncoated cerium oxide nanopigments are sold under the name "Colloidal Cerium Oxide" by the company Rhone-Poulenc.

The uncoated iron oxide nanopigments are sold, for example, by the company Arnaud under the names "Nanogard WCD 2002 (FE 45B)", "Nanogard Iron FE 45 EL AQ", "Nanogard FE 45R AQ" and "Nanogard WCD 2006 (FE 45R)" or by the company Mitsubishi under the name "TY-220", The coated iron oxide nanopigments are sold, for example, by the company Arnaud under the names "Nanogard WOO 2008 (FE 455 FN)", "Nanogard WCD 2009 (FE 45B 556)", "Nanogard FE 45 BL 345" and "Nanogard FE 45 BL" or by the company BASF under the name "Transparent Iron Oxide".

Mention may also be made of mixtures of metal oxides, especially of titanium dioxide and of cerium dioxide, including the silica-coated equal-weight mixture of titanium dioxide and of cerium dioxide, sold by the company Ikeda under the name "Sunveil A", and also the alumina, silica and silicone-coated mixture of titanium dioxide and of zinc dioxide, such as the product "M 261" sold by the company Kemira, or the alumina, silica and glycerol-coated mixture of titanium dioxide and of zinc dioxide, such as the product "M 211" sold by the company Kemira.

The nanopigments may be introduced into the compositions according to the invention in unmodified form or in the form of pigmentary paste, i.e. as a mixture with a dispersant, as described, for example, in document GB-A-2 206 339.

The sunscreen active is typically present in an amount of from about 1.0 to about 50% by weight, such as from about 5.0 to about 45% by weight, and from about 7.0 to about 40% by weight, based on the total weight of the composition.

The composition of the present invention may also contain agents for artificially tanning and/or browning the skin (self-tanning agents) and more particularly dihydroxyacetone (DHA). They are preferably present in amounts ranging from 0.1% to 10% by weight relative to the total weight of the composition.

The composition may also comprise standard cosmetic adjuvants chosen especially from fatty substances, organic solvents, ionic or nonionic, hydrophilic or lipophilic thickeners, softeners, humectants, opacifiers, stabilizers, emollients, silicones, antifoams, fragrances, preserving agents, anionic, cationic, nonionic, zwitterionic or amphoteric surfactants, active agents, fillers, propellants, acidifying or basifying agents, co-emulsifiers or any other ingredient usually used in cosmetics and/or dermatology.

Oils that may be mentioned include mineral oils (paraffin); plant oils (sweet almond oil, macadamia oil, grapeseed oil or jojoba oil); synthetic oils, for instance perhydrosqualene, fatty alcohols, fatty acids or fatty esters (for instance the $C_{12}$-$C_{15}$ alkyl benzoate sold under the trade name "Finsolv TN" of "Witconol TN" by the company Witco, octyl palmitate, isopropyl lanolate and triglycerides, including capric/caprylic acid triglycerides), oxyethylenated or oxypropylenated fatty esters and ethers; silicone oils (cyclomethicone and polydimethylsiloxanes, or PDMS) or fluoro oils, and polyalkylenes.

Among the organic solvents that may be mentioned are lower alcohols and polyols. These polyols may be chosen from glycols and glycol ethers, for instance ethylene glycol, propylene glycol, butylene glycol, dipropylene glycol or diethylene glycol.

Among the active agents that may be mentioned are:
antipollution agents and/or free-radical scavengers;
depigmenting agents and/or propigmenting agents;
antiglycation agents;
NO-synthase inhibitors;
agents for stimulating the synthesis of dermal or epidermal macromolecules and/or for preventing their degradation;
agents for stimulating fibroblast proliferation;
agents for stimulating keratinocyte proliferation;
muscle relaxants;
tensioning agents;
desquamating agents;
moisturizers;
anti-inflammatory agents;
agents acting on the energy metabolism of cells;
insect repellants;
substance P or CGRP antagonists.

Needless to say, a person skilled in the art will take care to select the optional additional compound(s) mentioned above and/or the amounts thereof such that the advantageous properties intrinsically associated with the compositions in accordance with the invention are not, or are not substantially, adversely affected by the envisaged addition(s).

The compositions according to the invention may be prepared according to techniques that are well known to those skilled in the art, in particular those intended for the preparation of emulsions of oil-in-water or water-in-oil type. They may be in particular in the form of a simple or complex emulsion (O/W, W/O, O/W/O or W/O/W emulsion) such as a cream or a milk, in the form of a gel or a cream-gel, or in the form of a lotion.

The present invention will be better understood from the examples that follow, all of which are intended for illustrative purposes only and are not meant to unduly limit the scope of the invention in any way.

EXAMPLES

Example 1

Inventive Composition

| Phase | Chemical Name/TradeName | % wt/wt |
|---|---|---|
| A-1 | Water | Q.S. |
|  | EDTA | 0.100 |
|  | Presevative | Q.S. |
| A-2 | Propylene glycol | 0.500 |
|  | Fomblin HC/P2-1000 ® ® | 0.200 |
| B | Avobenzone | 3.000 |
|  | Octocrylene | 5.000 |
|  | Benzophenone-3 | 6.000 |
|  | Octyl Salicylate | 5.000 |
|  | Homosalate | 15.000 |
|  | Inutec SP-1 | 0.700 |
| C | SPF Booster | 4.000 |
| D | Aesthetic Modifier | Q.S. |
| E | Isononyl isonanonoate | 1.500 |
|  | Xanthan Gum | 0.150 |
| F | Vit E | 0.100 |
| G | Aristoflex HMS | 0.125 |

Procedure:
1. In Main Kettle, heat and mix phase A-1 to 80 C.
2. While heating pre-mix Phase A-2 and add into Phase A-1
3. In a separate kettle, heat and mix phase B to 80 C. Mix well.
4. Add Phase C into Phase B and homogenized for 20 minutes.
5. Add Phase B/C into main kettle. Increase homogenization and mix well for 20-25 minutes.
6. Start cooling. Reduce homogenization to avoid aeration of batch.
7. At 60 C, add phase E. Mix well.
8. At 40 C add phase D. Mix well.
9. At 30 C add Phase F and Mix well.
10. At 30 C. add Phase G. Homogenized for 15 to 20 min.
11. Cool to room temperature.

Example 2

Stability Testing

| Phase | Chemical Name/TradeName | Inventive Composition % wt/wt | Comparative 1 % wt/wt | Comparative 2 % wt/wt | Comparative 3 % wt/wt |
|---|---|---|---|---|---|
| A-1 | Water | 44.975 | 44.975 | 44.975 | 44.975 |
|  | EDTA | 0.100 | 0.100 | 0.100 | 0.100 |
|  | Presevative | Q.S. | Q.S. | Q.S. | Q.S. |
| A-2 | Propylene glycol | 0.500 | 0.500 | 0.500 | 0.500 |
|  | Fomblin HC/P2-1000 ® ® | 0.200 | 0.200 | 0.200 | 0.200 |
| B | Avobenzone | 3.000 | 3.000 | 3.000 | 3.000 |
|  | Octocrylene | 5.000 | 5.000 | 5.000 | 5.000 |
|  | Benzophenone-3 | 6.000 | 6.000 | 6.000 | 6.000 |
|  | Octyl Salicylate | 5.000 | 5.000 | 5.000 | 5.000 |
|  | Homosalate | 15.000 | 15.000 | 15.000 | 15.000 |
|  | Co Emulsifier | 0.500 | 0.500 | 0.500 | 0.500 |
|  | Inutec SP-1 | 0.700 | 0.000 | 0.000 | 0.000 |
|  | Polyglyceryl-3 Methylglucose-distearate | 0.000 | 0.700 | 0.000 | 0.000 |
|  | Archidyl alcohol (and) Behenyl alcohol (and) Archidyl Glucoside | 0.000 | 0.000 | 0.700 | 0.000 |
|  | Glyceryl Stearate/PEG-100 Stearate | 0.000 | 0.000 | 0.000 | 0.700 |
| C | SPF Booster | 4.000 | 4.000 | 4.000 | 4.000 |
| D | Aesthetic Modifier | Q.S. | Q.S. | Q.S. | Q.S. |
| E | Isononyl isonanonoate | 1.500 | 1.500 | 1.500 | 1.500 |
|  | Xanthan Gum | 0.150 | 0.150 | 0.150 | 0.150 |
| F | Vitamin E | 0.100 | 0.100 | 0.100 | 0.100 |
| G | Aristoflex HMS | 0.125 | 0.125 | 0.125 | 0.125 |
| 12 week stability |  | Passed | Failed | Failed | Failed |

Stability testing was performed on the inventive composition and three comparative compositions. The three comparative compositions were prepared by varying the emulsifier of the inventive composition, Inutec SP-1, with the conventional emulsifiers of Polyglyceryl-3 Methylglucosedistearate, Archidyl alcohol (and) Behenyl alcohol (and) Archidyl Glucoside, and Glyceryl Stearate/PEG-100 Stearate. All four formulas were kept in the oven at 5°, 25°, 37° and 45° C. for 12 weeks and F/T for 10 cycles. Each week, the four formulas were removed from the oven after heating and allowed to cool down to room temperature and observed for product stability. The results showed that the inventive composition passed the stability test at the end of the 12 week testing period, while the three comparative compositions all failed stability testing by separating at 45° C.

Example 3

In Vitro Water Resistance Test

| Formula | Emulsifier system | Water resistance (in-vitro) | 12-weeks Stability |
|---|---|---|---|
| Inventive composition with no film former | Polyperfluoroethoxymethoxy-difluoroethyl PEG Phosphate, Inulin Lauryl Carbamate, Sucrose Stearate, Stearyl alcohol | 94.96% | Stable |
| Comparative 1 with no film former | PEG-100 Stearate/Glyceryl Stearate, Stearic Acid, Potassium Cetyl Phosphate, Stearyl alcohol | 73.98% | Stable |
| Comparative 2 with film former | PEG-100 Stearate/Glyceryl Stearate, Stearic Acid, Potassium Cetyl Phosphate, Stearyl alcohol | 98.72% | Stable |

The results from the in vitro water resistance test based on absorbance measurements of the test compositions after exposure to water show that the degree of water resistance by the inventive composition is comparable to that of the comparative sample 2 containing a film former and is significantly better than that of comparative sample 1 which did not contain a film former.

Example 4

In Vivo Water Resistance Test

| Formula | SPF (Static) | SPF (VWR) | % WR |
|---|---|---|---|
| Inventive Composition (with Fomblin HC/P2-1000 ®) | 57 | 55 | 96.50% |
| Control Composition (with Fomblin HC25) | 58 | 42 | 72.41% |

In vivo testing was also performed on two compositions to evaluate the effectiveness of the inventive composition as a sunscreen product by determining the Sun Protection Factor (SPF) on human skin using a Xenon arc solar simulator as the UV source. This was done by collecting data on the static SPF which means the SPF was checked after the application of the compositions on the panelists, but before the panelists/products were exposed to water. The very water resistance (VWR) SPF data was also collected and means the SPF was checked after the product was applied to the panelists and the panelists/products were subjected to water for 80 minutes. The results show that the inventive composition containing Fomblin HC/P2-1000® provides 96.50% water resistance. The second composition is a control containing Fomblin HC-25 (INCI name—Polyperfluoromethylisopropyl Ether) which is a different type of water repellent emulsifier, provides only 72.41% water resistance. The results show that the inventive composition containing Fomblin HC/P2-1000® performs better than the same composition using a different type of water repellent emulsifier.

Evaluation of the Properties of the Inventive Composition

An evaluation study was conducted on the skin of six Caucasian female panelists. Two of the panelists had dry skin, one had combination to dry skin, and the remaining three panelists had combination to oily skin types. The six panelists were required to apply both the inventive composition as well as a control composition, which is a product currently on the market, and give feedback regarding the product. When applying the inventive composition to their skin, the panelists noted that the inventive composition felt light and was very comfortable. It was also noted by the aesthetician that the inventive compositions appears to perform better than the control in terms of application, spreadability, penetration and the final skin feel.

A second evaluation study was also conducted on the skin of twelve panelists, ages 18+. The selection criteria for these panelists were based on individuals who participate in weekly outdoor activities and use a lotion sunscreen product with SPF 30 or higher on their face and body when participating in these activities. All twelve panelists gave a rating of "somewhat satisfied" to "very satisfied" to the inventive composition. The panelists were most satisfied with the inventive composition in terms of it being the appropriate color for a face and body sunscreen, pleasant and smooth product texture, very easy application, light feel on the skin, not feeling sticky on the skin, smooth skin feel, just the right amount of moisture, skin appearance (very shiny to somewhat matte), and comfortable skin feel.

Overall the product showed favorable results with the panelists, especially in terms of feel on the skin, comfort on the skin, and product texture.

What is claimed is:

1. A sunscreen composition comprising:
    (a) at least one oil- and water repellent emulsifier chosen from polyperfluoroethoxymethoxy difluoroethyl PEG phosphate;
    (b) at least one hydrophobically-modified emulsifier chosen from inulin lauryl carbamate;
    (c) at least one hydrophilic gelling agent; and
    (d) sunscreen actives,
    and wherein the composition is water-resistant, while not requiring the use of a hydrophobic film-former, and is a stable emulsion.

2. The sunscreen composition of claim 1, wherein the at least one oil- and water repellent emulsifier of (a) is present in an amount of from about 0.05 to about 1.0% by weight, based on the total weight of the composition.

3. The sunscreen composition of claim 1, wherein the at least one oil- and water repellent emulsifier of (a) is present in an amount of from about 0.05 to about 0.5% by weight, based on the total weight of the composition.

4. The sunscreen composition of claim 1, wherein the at least one hydrophobically-modified emulsifier of (b) is present in an amount of from about 0.1 to about 2.0% by weight, based on the total weight of the composition.

5. The sunscreen composition of claim 1, wherein the at least one hydrophobically-modified emulsifier of (b) is present in an amount of from about 0.5 to about 1.0% by weight, based on the total weight of the composition.

6. The sunscreen composition of claim 1, wherein the at least one hydrophilic gelling agent of (c) is chosen from carboxyvinyl polymers, polyacrylamides, 2-acrylamido-2-methylpropanesulfonic polymers and copolymers, cellulose-based derivatives, polysaccharides, gums, and mixtures thereof.

7. The sunscreen composition of claim 6, wherein the at least one hydrophilic gelling agent is ammonium acryloyldimethyltaurate/steareth-25 methacrylate crosspolymer.

8. The sunscreen composition of claim 6, wherein the at least one hydrophilic gelling agent is present in an amount of from about 0.05 to about 1.5% by weight, based on the total weight of the composition.

9. The sunscreen composition of claim 6, wherein the at least one hydrophilic gelling agent is present in an amount of from about 0.1 to about 0.5% by weight, based on the total weight of the composition.

10. A method of protecting a keratinous substrate from UV radiation comprising applying onto a surface of the keratinous substrate a composition containing:
    (a) at least one oil- and water repellent emulsifier chosen from polyperfluoroethoxymethoxy difluoroethyl PEG phosphate;
    (b) at least one hydrophobically-modified emulsifier chosen from inulin lauryl carbamate; and
    (c) at least one hydrophilic gelling agent, and (d) sunscreen actives,
    and wherein the composition is water-resistant, while not requiring the use of a hydrophobic film-former, and is a stable emulsion.

11. The method of claim 10, wherein the at least one oil- and water repellent emulsifier of (a) is present in an amount of from about 0.05 to about 1.0% by weight, based on the total weight of the composition.

12. The method of claim 10, wherein the at least one hydrophobically-modified emulsifier of (b) is present in an amount of from about 0.1 to about 2.0% by weight, based on the total weight of the composition.

13. The sunscreen composition of claim 10, wherein the at least one hydrophilic gelling agent of (c) is chosen from carboxyvinyl polymers, polyacrylamides, 2-acrylamido-2-methylpropanesulfonic polymers and copolymers, cellulose-based derivatives, polysaccharides, gums, and mixtures thereof.

14. The method of claim 13, wherein the at least one hydrophilic gelling agent of (c) is present in an amount of from about 0.05 to about 1.5% by weight, based on the total weight of the composition.

* * * * *